United States Patent
De Souza et al.

(10) Patent No.: US 10,688,088 B2
(45) Date of Patent: Jun. 23, 2020

(54) PHARMACEUTICAL COMPOSITION, USE OF MEFLOQUINE IN FIXED DOSE, AND METHOD FOR TREATING TUBERCULOSIS

(71) Applicant: FUNDACÃO OSWALDO CRUZ, Rio de Janeiro (BR)

(72) Inventors: Marcus Vinicius Nora De Souza, Rio de Janeiro (BR); Raoni Schroeder Borges Goncalves, Rio de Janeiro (BR); Maria Cristina Da Silva Lourenco, Rio de Janeiro (BR)

(73) Assignee: Fundacao Oswaldo Cruz, Rio de Janiero (BR)

( * ) Notice: Subject to any disclaimer, the term of this patent is extended or adjusted under 35 U.S.C. 154(b) by 0 days.

(21) Appl. No.: 15/771,941

(22) PCT Filed: Oct. 7, 2016

(86) PCT No.: PCT/BR2016/050254
§ 371 (c)(1),
(2) Date: Apr. 27, 2018

(87) PCT Pub. No.: WO2017/070763
PCT Pub. Date: May 4, 2017

(65) Prior Publication Data
US 2018/0318283 A1 Nov. 8, 2018

(30) Foreign Application Priority Data
Oct. 29, 2015 (BR) .............................. 20150274491

(51) Int. Cl.
| | | |
|---|---|---|
| *A61K 31/4709* | (2006.01) | |
| *A61K 31/4409* | (2006.01) | |
| *A61K 31/4965* | (2006.01) | |
| *A61K 31/5377* | (2006.01) | |
| *A61K 31/7036* | (2006.01) | |
| *A61K 31/133* | (2006.01) | |
| *A61K 31/496* | (2006.01) | |
| *A61P 31/06* | (2006.01) | |
| *A61K 47/02* | (2006.01) | |
| *A61K 47/10* | (2017.01) | |
| *A61K 47/20* | (2006.01) | |
| *A61K 47/26* | (2006.01) | |
| *A61K 47/32* | (2006.01) | |
| *A61K 47/38* | (2006.01) | |
| *A61K 47/44* | (2017.01) | |
| *A61K 9/10* | (2006.01) | |
| *A61K 9/00* | (2006.01) | |
| *A61K 31/42* | (2006.01) | |
| *A61K 31/513* | (2006.01) | |
| *A61K 31/606* | (2006.01) | |

(52) U.S. Cl.
CPC ........ *A61K 31/4709* (2013.01); *A61K 31/133* (2013.01); *A61K 31/4409* (2013.01); *A61K 31/496* (2013.01); *A61K 31/4965* (2013.01); *A61K 31/5377* (2013.01); *A61K 47/02* (2013.01); *A61K 47/10* (2013.01); *A61K 47/20* (2013.01); *A61K 47/26* (2013.01); *A61K 47/32* (2013.01); *A61K 47/38* (2013.01); *A61K 47/44* (2013.01); *A61P 31/06* (2018.01); *A61K 9/0095* (2013.01); *A61K 9/10* (2013.01); *A61K 31/42* (2013.01); *A61K 31/513* (2013.01); *A61K 31/606* (2013.01); *A61K 31/7036* (2013.01); *A61K 2300/00* (2013.01)

(58) Field of Classification Search
None
See application file for complete search history.

(56) References Cited

FOREIGN PATENT DOCUMENTS

| WO | 2010026526 A1 | 3/2010 | |
|---|---|---|---|
| WO | WO-2010026526 A1 * | 3/2010 | ......... A61K 31/4409 |
| WO | 2012068560 A2 | 5/2012 | |

OTHER PUBLICATIONS

Danelishvili, L., Wu, M., Young, L. S., & Bermudez, L. E. (2005). Genomic approach to identifying the putative target of and mechanisms of resistance to mefloquine in mycobacteria. Antimicrobial agents and chemotherapy, 49(9), 3707-3714. (Year: 2005).*

Mao, J., Wang, Y., Wan, B., Kozikowski, A. P., & Franzblau, S. G. (2007). Design, Synthesis, and Pharmacological Evaluation of Mefloquine-Based Ligands as Novel Antituberculosis Agents. ChemMedChem: Chemistry Enabling Drug Discovery, 2(11), 1624-1630. (Year: 2007).*

Lenaerts, A. J., et al. (2009). Mefloquine, moxifloxacin and pyrazinamide is a triple-drug alternative to isoniazid-and rifampin-containing regimens for treatment of tuberculosis in mice, abstr. B-1873. Abstr. 49th Intersci. In Conf. Antimicrob.Agents Chemother., San Francisco, CA. (Year: 2009).*

"World Malaria Report 2011", World Health Organization 2011, WHO Library Cataloguing-in-Publication Data, pp. 1-278.

Bermudez, Luiz E. et al., "Mefloquine, Moxifloxacin, and Ethambutol Are a Triple-Drug Alternative to Macrolide-Containing Regimens for Treatment of *Mycobacterium avium* Disease", The Journal of Infectious Diseases Brief Report (2003), Infectious Diseases Society of America, pp. 1977-1980.

Bermudez, Luiz E. et al., "SRI-286, a Thiosemicarbazole, in Combination with Mefloquine and Moxifloxacin for Treatment of Murine *Mycobacterium avium* Complex Disease", Antimicrobial Agents and Chemotherapy, Sep. 2004, vol. 48, No. 9, pp. 3556-3558.

Goncalves, Raoni S.B., et al., "Mefloquine-oxazolidine derivatives, derived from mefloquine and arenecarbaldehydes: in vitro activity including against the multidrug-resistant tuberculosis strain T113", Bioorganic & Medicinal Chemistry, journal homepage: www.elsevier.com/locate/bmc, (2012), pp. 243-248.

(Continued)

*Primary Examiner* — Dale R Miller
(74) *Attorney, Agent, or Firm* — Dorsey & Whitney LLP

(57) ABSTRACT

This invention concerns the use of mefloquine in relation to *Mycobacterium tuberculosis*. This invention also concerns the combination of mefloquine with drugs used in first and second choice treatment of tuberculosis, achieving a reduction in the treatment period of tuberculosis (TB) and the treatment of multi-drug resistant tuberculosis (MDR-TB).

3 Claims, 2 Drawing Sheets

(56) References Cited

OTHER PUBLICATIONS

Figure 1:
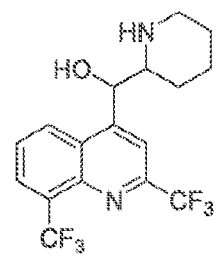
Figure 2A:
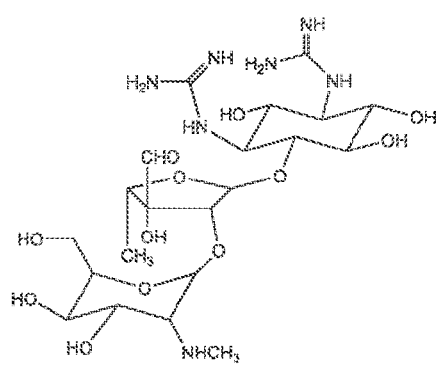
Figure 2B:
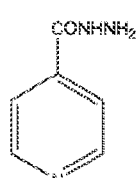
Figure 2C:
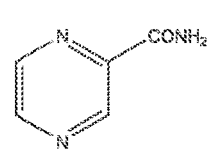
Figure 2D:
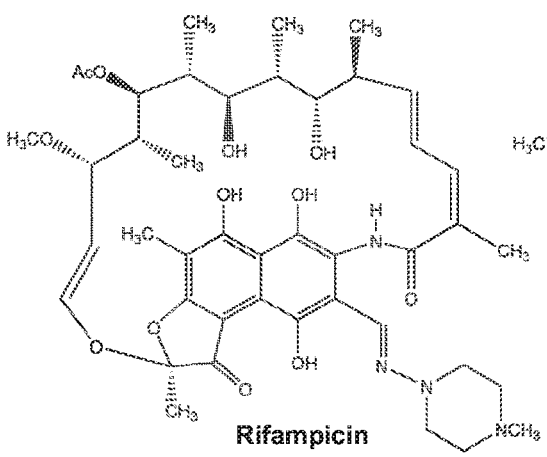
Figure 2E:
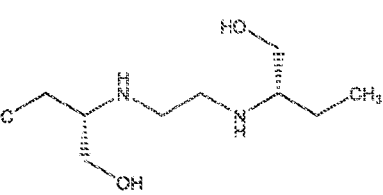
Figure 2F:
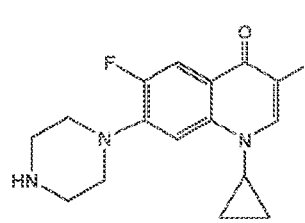
Figure 2G:
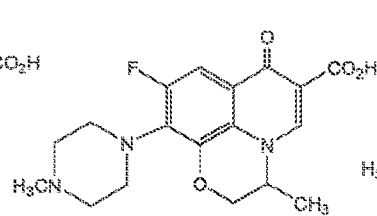
Figure 2H:
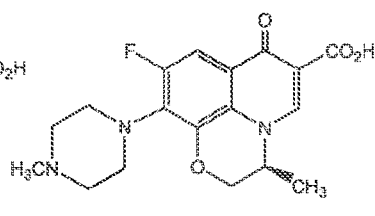
Figure 2I:
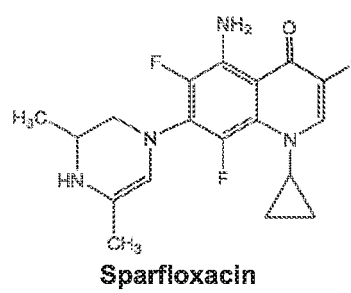
Figure 2J:
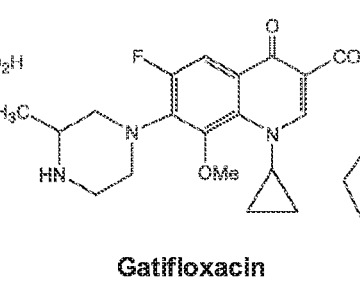
Figure 2K:
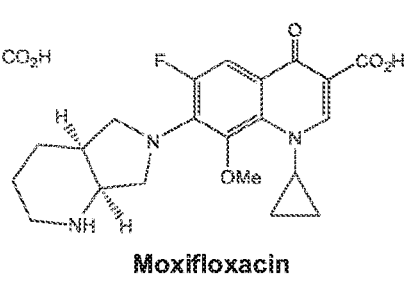
Figure 2L:
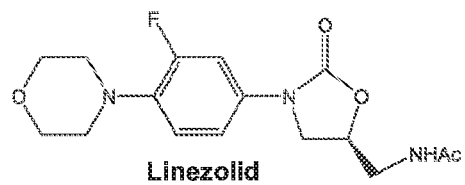

Fu, L.M., et al. "Is Mycobacterium tuberculosis a closer relative to Gram-positive or Gram-negative bacterial pathogens?", Elsevier Science Ltd., Pacific Tuberculosis and Cancer Research Organization, Los Angeles, California, U.S.A., 2002, 85-90.
Jayapraskash, Sarva et al., "Design, Synthesis, and SAR Studies of Mefloquine-Based Ligands as Potential Antituberculosis Agents", ChemMedChem (2006), Wiley-VCH Verlag GmbH & Co. KGaA, Weinheim, pp. 593-597.
Keri, Rangappa S., et al. "Quinoline: A promising antitubercular target", Biomedicine & Pharmacotherapy 68 (2014), Elsevier Masson SAS, pp. 1161-1175.
Kunin, C.M., et al., "Antimicrobial Activities of Mefloquine and a Series of Related Compounds", Antimicrobial Agents and Chemotherapy, Apr. 2000, vol. 44, No. 4, pp. 848-852.
Mao, Jialin et al. "Design, Synthesis, and Pharmacological Evaluation of Mefloquine-Based Ligands as Novel Antituberculosis Agents", DOI: 10.1002/Chem MedChem (2007), Wiley-VCH Verlag GmBH & Co. KGA, Weinheim, pp. 1624-1630.
Rey-Jurado, Emma, et al., "Synergistic effect of two combinations of antituberculous drugs against *Mycobacterium tuberculosis*", Tuberculosis 92 (2012), Elsevier Ltd., pp. 260-263.
Rodriguez Diaz, Juan et al., "Synergic activity of fluoroquinolones and linezolid against *Mycobacterium tuberculosis*", Elsevier International Journal of Antimicrobial Agents (2003), pp. 354-356.
Young, Lowell S., "Reconsidering Some Approved Antimicrobial Agents for Tuberculosis", Antimicrobial Agents and Chemotherapy, Nov. 2009, vol. 53, No. 11, p. 4577-4579.

\* cited by examiner

Mefloquine

Streptomycin

Isoniazid

Pyrazinamide

Rifampicin

Ethambutol

Ciprofloxacin

Ofloxacin

Levofloxacin

Sparfloxacin

Gatifloxacin

Moxifloxacin

Linezolid

PHARMACEUTICAL COMPOSITION, USE OF MEFLOQUINE IN FIXED DOSE, AND METHOD FOR TREATING TUBERCULOSIS

CROSS-REFERENCE TO RELATED APPLICATIONS

The present application is a U.S. National Stage entry under 35 U.S.C. § 371 of International Application No. PCT/BR2016/050254, filed on Oct. 7, 2016, which claims the benefit of Brazilian Application No. 1020150274491, filed on Oct. 29, 2015, each of which is hereby incorporated herein by reference in its entirety.

FIELD OF INVENTION

This invention concerns, in its broadest conception, the use of mefloquine (MFL) in relation to *Mycobacterium tuberculosis*.

BASES OF THE INVENTION

Tuberculosis (TB) is an ancient infectious disease caused by *Mycobacterium tuberculosis* and continues to be the main cause of death by infectious disease around the world. *Mycobacterium tuberculosis* was discovered and identified in 1882 by Robert Koch and, in honor of him, it is also known as Koch's *bacillus* (BK).

The treatment of TB is based on a fixed combined dose of four drugs: rifampicin (RIF), isoniazid (INH), pyrazinamide (PYR) and ethambutol (ETB). The fixed dose regime is designed not only to prevent the symptoms caused by active TB, but also to prevent the development of resistant bacteria, frequently observed in the case of monotherapy. However, the period of treatment is long (six months), and the appearance of side effects in individuals is very common. As a consequence of this, despite the fact that the current treatment has reduced the number of deaths caused by TB, high levels of lapsing and interruption have been observed. This fact has directly contributed to the emergence of resistant strains of *Mycobacterium tuberculosis*.

Currently, the World Health Organization (WHO) classifies resistance to TB at two levels: multidrug-resistant tuberculosis (MDR-TB) and extensively drug-resistant tuberculosis (XDR-TB). MDR-TB is caused by bacteria that are resistant at least to INH and RIF. In the case of XDR-TB, the bacteria are resistant to INH and RIF, as well as one fluoroquinolone and an injectable drug used in second-choice treatment (amikacin, kanamycin and capreomycin). These forms of TB do not respond to the standard six month treatment, its being necessary to use more toxic and less effective drugs. As a result, in addition to being prolonged (around two years), the treatment also becomes much more costly.

With the appearance of HIV, tuberculosis chemotherapy has undergone great changes. The appearance of multi-drug resistant strains, above all those resistant to rifampicin and isoniazid, has created many public health problems. As a result, it has been necessary to resort to new medicaments which has led to the classification of anti-tuberculosis drugs in two groups:
(1) the primary ones (first line or first choice) which are more potent and less toxic; and,
(2) the secondary ones (second line or second choice) which are less potent and more toxic.

The drugs characterized as "first line" include isoniazid (INH), rifampicin (RIF), ethambutol (ETB) and pyrazinamide (PYR); and the second line drugs include streptomycin (SM) ethionamide (Et), aminosalicylic acid (Aa), cycloserine (Cs), amikacin (Am), kanamycin (Cn), capreomycin (Cp) and linezolid (L).

Mao et al., [ChemMedChem. 2007 Nov.; 2(11):1624-30. Design, synthesis, and pharmacological evaluation of mefloquine-based ligands as novel antituberculosis agents. Mao J, Wang Y, Wan B, Kozikowski A P, Franzblau S G.] mention that mefloquine analogues were developed and that they were evaluated regarding anti-TB activity against *Mycobacterium tuberculosis* H37 Rv.

Lowell S. Young et al. [Antimicrob. Agents Chemother. Nov. 2009 vol. 53 no. 11 4577-4579, Reconsidering Some Approved Antimicrobial Agents for Tuberculosis, Published ahead of print 8 Sep. 2009, doi: 10.1128/AAC.00887-09] report that mefloquine, which is active against strains resistant to cloroquine, possesses bactericidal activity against *Mycobacterium Avium* Complex (MAC), the most common infection by nontuberculosis mycobacteria. A single report of a human case described the successful treatment of a patient [rendered] resistant to MAC disease through the addition of linezolid and mefloquine to other anti-Mac agents, though the first compound has limitations in long term therapy. The article speculated that mefloquine also has an effect against *M. tuberculosis* and may be a substitute for isoniazid and rifampicin.

Raoni et al., [in Bioorganic & Medicinal Chemistry, Volume 20, Issue 1, 1 Jan. 2012, Pages 243-248. Mefloquine-oxazolidine derivatives, derived from mefloquine and arenecarbaldehydes: In vitro activity including against the multidrug-resistant tuberculosis strain T113] present a study where new mefloquine-oxazolidine derivatives show improved anti-tuberculosis activity in relation to first line drugs.

It is worth highlighting that the studies of Mao at al. e Raoni at al. are reports of modifications made to the mefloquine molecule (new substances) which have still not undergone a series of tests such as animal model and toxicological tests. Only in vitro tests have been done and they were not tested with other drugs, which is to say they are basic studies in the development of new drugs.

The study of Lowell S. Young et al. offers a good example of the potential of mefloquine in combination with other drugs, in this case using linezolid. However, the author used only linezolid which has not yet been approved as an anti-TB drug.

In this context, the development of new, more efficient and less toxic combinations which also contribute to reducing the treatment time of different forms of TB, with reduced side effects, is considered a global priority in the public health sphere.

SUMMARY OF THE INVENTION

This invention presents a wholly different and nonobvious concept in relation to the other studies reported in the literature, which is a combination of different drugs used in the treatment of tuberculosis with mefloquine demonstrating that this drug presents an important synergism when combined with other anti-TB drugs, presenting significant potential in the development of a new combination (medicament) in the treatment of resistant tuberculosis.

This invention concerns, in its broadest conception, the use of mefloquine in relation to *Mycobacterium tuberculosis* to combat tuberculosis.

This invention also concerns the use of mefloquine against *Mycobacterium tuberculosis* combined with anti-tuberculosis agents for more effective treatment of tuberculosis.

This invention presents a composition for the treatment of tuberculosis.

BRIEF DESCRIPTION OF THE FIGURES

FIG. 1 shows the chemical structure of the drug mefloquine.

FIGS. 2A-2L show the chemical structures of some drugs used in combination with mefloquine.

DETAILED DESCRIPTION OF THE INVENTION

In the search for new treatments to combat tuberculosis (TB), the hereby inventors identified mefloquine (MFL) as being potentially useful in the treatment of TB.

Among the significant aspects that were considered by the inventors in the selection of mefloquine for use in a combined fixed dose formulation for the treatment of tuberculosis, were: (i) its relatively long half-life; (ii) that it is well-tolerated by patients with HIV; (iii) that it did not present medical interactions with anti-retrovirals such as protease inhibitors; (iv) that it presented good gastrointestinal absorption; and, (v) that it concentrates mainly in the lungs, the organ most affected by *M. tuberculosis.*

MFL is currently used in malaria prophylaxis (World Malaria Report). However, MFL is also active against different species of Gram-positive bacteria (Kunin C M et al). Nevertheless, Fu L M et al. report that the phylogenetic position of *Mycobacterium tuberculosis* in relation to other bacteria is controversial. The cell wall of *Mycobacterium tuberculosis* has characteristics of both Gram-positive and Gram-negative bacteria. In the genome tree constructed based on the conserved gene content, *M. tuberculosis* is more closely related to Gram-negative bacteria than Gram-positive bacteria.

Even though the state of the art is controversial, as described above, the inventors continued their search to understand the effect of mefloquine in the treatment of tuberculosis, especially when combined with other drugs.

The inventors' search revealed a synergic effect of the combination of mefloquine with first line and second line drugs used in the treatment of tuberculosis.

Thus, this invention concerns the use of mefloquine in relation to *Mycobacterium tuberculosis.*

The invention also encompasses the combination of mefloquine with drugs used in first and second choice treatment of tuberculosis, achieving a potential reduction in the treatment period of the tuberculosis (TB) and in the treatment of multi-drug resistant tuberculosis (MDR-TB).

It is also an objective of this invention to provide an effective combination containing mefloquine to treat tuberculosis that includes varieties of *Mycobacterium tuberculosis* which are multiply resistant to drugs used in the treatment of tuberculosis.

This invention presents a pharmaceutical composition for treating tuberculosis in a mammal that encompasses the administration, to said mammal in need thereof, of an effective quantity of mefloquine in combination with agents effective in the treatment of tuberculosis.

The pharmaceutical preparations used in accordance with this invention are prepared by mixing one or more agents effective in the treatment of tuberculosis with mefloquine.

The proportions used both of mefloquine and the drugs (agents useful in the treatment of tuberculosis) used in the pharmaceutical composition of this invention vary from 0.01-10.

The number of drugs combined with mefloquine is a maximum of three drugs.

This invention shall now be described with reference to the following examples which should not be interpreted as limiting the scope of the invention.

Materials and Methods

1.1 *Mycobacterium Tuberculosis*

The following strains of *M. tuberculosis* were used:

standard strain *M. tuberculosis* H37 Rv (ATCC 27294);

resistant strain *M tuberculosis* T3609, resistant to ofloxacin (OFX) and streptomycin; and, multi-resistant strain T113, resistant to isoniazid (INH), rifampicin (RIF), ethambutol (ETB) and ofloxacin (OFX).

All the strains belong to the collection of the laboratory of Biotechnology and Biotests of the Evandro Chagas Institute of Clinical Research (*Bacteriologia e Bioensaio do Instituto de Pesquisa Clinica Evandro Chagas—IPEC*) of the Oswaldo Cruz Foundation.

1.2 Substances Used

In the tests carried out a minimum inhibitory concentration (MIC) of mefloquine was used in relation to the strains of *M. tuberculosis* previously mentioned here (item 1.1). Mefloquine was tested in combination with:

first choice drugs: isoniazid (INH), pyrazinamide (PYR), rifampicin (RIF) and ethambutol (ETB).

second choice drugs in the treatment of tuberculosis.

linezolid (LYN).

fluoroquinolones: gatifloxacin (GAT), moxifloxacin (MCX), sparfloxacin (SPR), ofloxacin (CFX), ciprofloxacin (CPX) and levofloxacin (LVX).

1.3 Proportions and Number of Substances Used

The proportions used both of mefloquine and the drugs used varied from 0.01-10. The number of drugs combined with mefloquine is a maximum of three.

1.3 Proportions and Numbers of Substances Used

The proportions used both of mefloquine and the drugs used varied from 0.01-10 p/p. The number of drugs combined with mefloquine is a maximum of three.

| Combination | $MIC_{combination}$ | Proportion |
|---|---|---|
| Mefloquine | 12.5 μg/mL | — |
| Mefloquine + Linezolid + Ofloxacin + Streptomycin | 0.01 μg/mL | (1.0-1.0-1.0-1.0) |
| Mefloquine + Moxifloxacin + Ethionamide + Kanamycin | 0.20 μg/mL | (0.5-0.5-1.0-1.0) |

1.4 Determination of the Minimum Inhibitory Concentration (MIC)

The anti-tuberculosis activities were determined against *M. tuberculosis* in medium 7H9 and the MIC values were determined using the Alamar Blue (MABA) colorimetric method.

1.5 Determination of Synergism Between the Substances

The synergic interactions between the drugs tested were determined through the Fractional Inhibitory Concentration Index (FIC) index, a method widely accepted and used by the scientific community (Guidelines of American Society for Microbiology). The calculations of the FIC were made using the following formula:

Calculation of the FIC (MIC of substance $A$, tested in combination)/MIC of substance $A$, tested alone+(MIC of substance $B$, tested in combination)/MIC of substance $B$, tested alone)

The interactions are evaluated as follows:
FIC≤0.5→synergic interactions
0.5<FIC≤4.0→additive interactions
FIC>4.0→antagonistic interactions

Example 1

Example 1 presents the results (Tables 1A and 1B) of the best combinations of the drug mefloquine with first choice drugs in the treatment of tuberculosis.

TABLE 1A

STRAIN H37RV - STANDARD STRAIN

| Combination | MIC$_{combination}$ | FIC | Proportion |
|---|---|---|---|
| Mefloquine | 12.5 µg/mL | — | — |
| Mefloquine + Pyrazinamide | 6.25 µg/mL | 0.3 | 0.5-1.0 |
| Mefloquine + Isoniazid | 0.20 µg/mL | 0.5 | 1.0-1.0 |

TABLE 1B

STRAIN T3609 - RESISTANT TO OFLOXACIN AND STREPTOMYCIN

| Combination | MIC$_{combination}$ | FIC | Proportion |
|---|---|---|---|
| Mefloquine | 25 µg/mL | — | — |
| Mefloquine + Isoniazid | 0.03 µg/mL | 0.03 | 1.0-1.0 |

Example 2

Example 2 presents the results (Tables 2A and 2B) highlighting the best combinations between MFL and different second choice drugs, the fluoroquinolones and linezolid (LYN).

TABLE 2A

STRAIN T3609 - RESISTANT TO OFLOXACIN AND STREPTOMYCIN

| Combination | MIC$_{combination}$ | FIC | Proportion |
|---|---|---|---|
| Mefloquine + Gatifloxacin | 0.62 µg/mL | 0.5 | 1.0-0.5 |
| Mefloquine + Moxifloxacin | 1.25 µg/mL | 0.5 | 1.0-0.5 |
| Mefloquine + Sparfloxacin | 1.25 µg/mL | 0.5 | 1.0-0.5 |

TABLE 2B

STRAIN T113 - RESISTANT TO ISONIAZID, RIFAMPICIN, ETHAMBUTOL AND OFLOXACIN

| Combination | MIC$_{combination}$ | FIC | Proportion |
|---|---|---|---|
| Mefloquine | 25 µg/mL | — | — |
| Mefloquine + Ofloxacin | 1.25 µg/mL | 0.5 | 1.0-0.5 |
| Mefloquine + Ciprofloxacin | 0.62 µg/mL | 0.5 | 1.0-0.5 |
| Mefloquine + Levofloxacin | 0.62 µg/mL | 0.5 | 1.0-0.5 |

Example 3

The MICs of MFL, of each drug tested alone (MIC 1) and of each drug tested in combination (MIC 2), are expressed in Tables 3 and 4.

TABLE 3

COMBINATIONS OF MFL AND DIFFERENT FLUOROQUINOLONES.

| | MFL + GAT | | | | | MFL + MOX | | | | |
|---|---|---|---|---|---|---|---|---|---|---|
| | MFL | | GAT | | | MFL | | MOX | | |
| Strain[a] | MIC 1 | MIC 2 | MIC 1 | MIC 2 | FIC | MIC 1 | MIC 2 | MIC 1 | MIC 2 | FIC |
| H37Rv | 12.5 | 0.12 | 0.12 | 0.12 | 1.0 | 12.5 | 0.15 | 0.25 | 0.15 | 0.6 |
| T3609 | 12.5 | 0.31 | 0.62 | 0.31 | 0.5 | 12.5 | 0.62 | 1.25 | 0.62 | 0.5 |
| T113 | 12.5 | 0.15 | 0.12 | 0.15 | 1.3 | 12.5 | 0.31 | 0.25 | 0.31 | 1.3 |

| | MFL + SPR | | | | | MFL + OFX | | | | |
|---|---|---|---|---|---|---|---|---|---|---|
| | MFL | | SPR | | | MFL | | OFX | | |
| Strain[a] | MIC 1 | MIC 2 | MIC 1 | MIC 2 | FIC | MIC 1 | MIC 2 | MIC 1 | MIC 2 | FIC |
| H37Rv | 12.5 | 0.12 | 0.12 | 0.12 | 1.0 | 12.5 | 0.62 | 1.25 | 0.62 | 0.5 |
| T3609 | 12.5 | 0.62 | 1.25 | 0.62 | 0.5 | 12.5 | 2.5 | 5.0 | 2.5 | 0.7 |
| T113 | 12.5 | 0.12 | 0.12 | 0.12 | 1.0 | 12.5 | 0.62 | 1.25 | 0.62 | 0.5 |

TABLE 3-continued

COMBINATIONS OF MFL AND DIFFERENT FLUOROQUINOLONES.

| | MEF + CPX | | | | | MEF + LVX | | | | |
|---|---|---|---|---|---|---|---|---|---|---|
| | MFL | | CPX | | | MFL | | LVX | | |
| Strain[a] | MIC 1 | MIC 2 | MIC 1 | MIC 2 | FIC | MIC 1 | MIC 2 | MIC 1 | MIC 2 | FIC |
| H37Rv | 12.5 | 0.62 | 0.62 | 0.62 | 1.0 | 12.5 | 0.62 | 0.62 | 0.62 | 1.0 |
| T3609 | 12.5 | 3.12 | 5.00 | 3.12 | 0.9 | 12.5 | 2.50 | 2.50 | 2.50 | 1.2 |
| T113 | 12.5 | 0.31 | 0.62 | 0.31 | 0.5 | 12.5 | 0.31 | 0.62 | 0.31 | 0.5 |

MIC 1: MIC of the substance tested alone/MIC 2: MIC of the substance tested in combination.
GAT—gatifloxacin,
MOX—moxifloxacin,
SPR—sparfloxacin,
OFX—ofloxacin,
CPX—ciprofloxacin,
LVX—levofloxacin

TABLE 4

COMBINATIONS OF MFL AND LYN AND DIFFERENT DRUGS
USED IN THE FIRST CHOICE TREATMENT OF TB.

| | MFL + PYR | | | | | MFL + ETB | | | | |
|---|---|---|---|---|---|---|---|---|---|---|
| | MFL | | PYR | | | MFL | | ETB | | |
| Strain[a] | MIC 1 | MIC 2 | MIC 1 | MIC 2 | FIC | MIC 1 | MIC 2 | MIC 1 | MIC 2 | FIC |
| H37Rv | 12.5 | 3.12 | 100 | 3.12 | 0.3 | 12.5 | 1.25 | 1.25 | 1.25 | 1.1 |
| T3609 | 12.5 | 0.62 | >100 | | — | 12.5 | N.D | N.D. | N.D. | N.D. |
| T113 | 12.5 | 0.62 | >100 | | — | 12.5 | 12.5 | 25.0 | 12.5 | 1.5 |

| | MFL + INH | | | | | MFL + LYN | | | | |
|---|---|---|---|---|---|---|---|---|---|---|
| | MFL | | INH | | | MFL | | LYN | | |
| Strain[a] | MIC 1 | MIC 2 | MIC 1 | MIC 2 | FIC | MIC 1 | MIC 2 | MIC 1 | MIC 2 | FIC |
| H37Rv | 12.5 | 0.10 | 0.20 | 0.10 | 0.5 | 12.5 | 0.62 | 0.62 | 0.62 | 1.0 |
| T3609 | 12.5 | 0.015 | 0.5 | 0.015 | 0.03 | 12.5 | N.D | N.D | N.D | N.D |
| T113 | 12.5 | 3.12 | 6.25 | 3.12 | 0.7 | 12.5 | 0.31 | 0.50 | 0.31 | 0.6 |

MIC 1: MIC of the substance tested alone/MIC 2: MIC of the substance tested in combination.
INH—isoniazid,
PYR—pyrazinamide,
ETB—ethambutol,
LYN—linezolid
N.D.—not determined When combined with the first choice drugs, three synergic interactions were observed: MFL+PYR and MFL+INH against the strain H37 Rv and a strong synergic interaction (FIC=0.03) between MFL and INH in relation to strain T3609. INH and PYR play a fundamental role in the treatment of TB. However, these drugs act in different phases of the development of M. tuberculosis. INH has a bactericide effect on the bacteria that are in growth, while PYR possesses a sterilizing effect and acts on the microorganisms that are latent.

In the light of the results hereby presented, it can be observed that mefloquine presented the same MIC in relation to all the strains—there is no cross-resistance. In addition to this, no antagonistic reaction of the mefloquine was observed in the combinations.

The pharmaceutical composition of this invention may be in any form that is usually used to administer the drug for therapeutic purposes. Thus, the composition may be in the form of tablets, capsules, syrups, liquid suspensions, elixirs, finely divided particles and similar substances. The pharmaceutical composition of this invention may include flavorings, colorings, and sweeteners or mixtures thereof.

The pharmaceutical composition of this invention may also include excipients selected from the group consisting of microcrystalline cellulose, lactose, crospovidone, corn starch, amino calcium alginate, poloxamer (polyoxyethylene-polyoxypropylene copolymer), talc, magnesium stearate, sodium lauryl sulfate, calcium stearate, sodium carboxymethylcellulose, magnesium carbonate, carnauba wax, colophony, white beeswax, paraffin, sugar coating, acacia, gelatin, kaolin, titanium dioxide (E171), colloidal silicon dioxide, polyvinylpyrrolidone K30, sucrose, Sunset Yellow (E110).

So the inventors demonstrated the synergic effect of the combination of mefloquine with the first and second line drugs used in the treatment of tuberculosis and multi-drug resistant tuberculosis.

This invention is not limited to the materializations shown here, but is in accordance with a broad scope consistent with the principles and new aspects hereby described.

It should be understood that the examples and materializations hereby described are merely for illustrative purposes and that various modifications or alterations based thereon will occur to those skilled in the art and should be included within the claim scope.

REFERENCES (1) World Malaria Report 2011, available at www.who.int/malaria.
(2) Kunin, C. M.; Ellis, W. Y. Antimicrob Agents Chemother. 2000, 44(4); 848-852.
(3) Tuberculosis (Edinb) 2002; 82 (2-3); 85-90. Is *Mycobacterium tuberculosis* a closer relative to Gram-positive or Gram-negative bacterial pathogens? Fu L M; Fu-Liu C S.
(4) Guidelines of American Society for Microbiology. Disponível em www.aac.asm).

The invention claimed is:

1. A pharmaceutical composition comprising:
   mefloquine;
   pyrazinamide; and
   one or more excipients,
   wherein the ratio of mefloquine to pyrazinamide is about 0.5 to about 1.0.

2. A pharmaceutical composition comprising:
   mefloquine;
   isoniazid; and
   one or more excipients,
   wherein the ratio of mefloquine to isoniazid is about 1.0 to about 1.0.

3. A pharmaceutical composition comprising:
   (a) mefloquine,
   (b) at least one, and a maximum of three, drugs selected from the group consisting of gatifloxacin, moxifloxacin, sparfloxacin, ofloxacin, ciprofloxacin, and levofloxacin; and
   one or more excipients,
   wherein the ratio of (a) to (b) is about 1.0 to about 0.5.

* * * * *